US012812327B2

(12) United States Patent
Gürsoy et al.

(10) Patent No.: US 12,812,327 B2
(45) **Date of Patent: *Nov. 24, 2026**

(54) BLOCKCHAIN SOLUTION FOR HARMONIZED STORAGE OF CLINICAL AND GENETIC DATA

(71) Applicant: THE TRUSTEES OF COLUMBIA UNIVERSITY IN THE CITY OF NEW YORK, New York, NY (US)

(72) Inventors: Gamze Gürsoy, New York, NY (US); Ahmed Elhussein, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/195,797

(22) Filed: May 1, 2025

(65) Prior Publication Data

US 2026/0082175 A1 Mar. 19, 2026

Related U.S. Application Data

(63) Continuation of application No. 18/419,923, filed on Jan. 23, 2024, now Pat. No. 12,369,010.

(Continued)

(51) Int. Cl.

*G06F 16/23* (2019.01)
*G06F 16/22* (2019.01)

(Continued)

(52) U.S. Cl.

CPC ........ *H04W 4/021* (2013.01); *G06F 16/2272* (2019.01); *G06F 16/2379* (2019.01); *G06F 16/245* (2019.01); *G16H 50/70* (2018.01); *H04W 4/023* (2013.01); *H04W 52/0203* (2013.01); *H04W 4/02* (2013.01); *H04W 4/027* (2013.01); *H04W 4/06* (2013.01);

(Continued)

(58) Field of Classification Search

None

See application file for complete search history.

(56) References Cited

U.S. PATENT DOCUMENTS

| | | | |
|---|---|---|---|
| 7,152,785 | B2 | 12/2006 | Metz et al. |
| 7,624,029 | B1 | 11/2009 | Ghouri |

(Continued)

OTHER PUBLICATIONS

Dedeturk et al., "Blockchain for genomics and healthcare: a literature review, current status, classification and open issues," Peer J 9:e12130 (2021) 35 pgs.

(Continued)

*Primary Examiner* — Eliyah S. Harper

(74) *Attorney, Agent, or Firm* — Baker Botts L.L.P.

(57) ABSTRACT

A method for practicing precision medicine comprising providing, to a blockchain platform, each of clinical data and genetic data, providing the blockchain platform, the blockchain platform having a first data structure comprising clinical data and a second data structure comprising genetic data, harmonizing the first and second data structures, creating at least one cohort based on the harmonized first and second data structures, and identifying at least one relationship between the clinical data and the genetic data in each of the at least one cohort.

14 Claims, 7 Drawing Sheets

Related U.S. Application Data

(60) Provisional application No. 63/481,049, filed on Jan. 23, 2023.

(51) Int. Cl.

| | |
|---|---|
| ***G06F 16/245*** | (2019.01) |
| ***G16H 50/70*** | (2018.01) |
| ***H04W 4/02*** | (2018.01) |
| ***H04W 4/021*** | (2018.01) |
| ***H04W 52/02*** | (2009.01) |
| *H04W 4/06* | (2009.01) |
| *H04W 4/33* | (2018.01) |
| *H04W 4/80* | (2018.01) |

(52) U.S. Cl.
CPC ................ *H04W 4/33* (2018.02); *H04W 4/80* (2018.02); *Y02D 30/70* (2020.08)

(56) References Cited

U.S. PATENT DOCUMENTS

| | | | |
|---|---|---|---|
| 7,899,764 B2 | 3/2011 | Martin et al. | |
| 8,175,896 B2 | 5/2012 | Dalton et al. | |
| 9,092,391 B2 | 7/2015 | Stephan et al. | |
| 11,139,081 B2 * | 10/2021 | Tran | G06Q 30/0206 |
| 2018/0001184 A1 * | 1/2018 | Tran | G16H 50/20 |
| 2018/0005417 A1 * | 1/2018 | Schieke | G06T 11/006 |
| 2019/0026425 A1 * | 1/2019 | Downs | G16H 10/40 |
| 2019/0238320 A1 * | 8/2019 | Mccurry | G06F 21/64 |
| 2020/0242984 A1 * | 7/2020 | Salem | B64B 1/58 |
| 2020/0251213 A1 * | 8/2020 | Tran | G06N 20/20 |
| 2020/0327250 A1 * | 10/2020 | Wang | G06N 20/00 |
| 2021/0020285 A1 * | 1/2021 | Hall | G16H 15/00 |
| 2022/0139566 A1 * | 5/2022 | Gardina | G16B 50/20 705/2 |
| 2024/0266074 A1 * | 8/2024 | Smurro | G16H 80/00 |

OTHER PUBLICATIONS

U.S. Appl. No. 18/419,923 (US 2024/0395418), filed Jan. 23, 2024 (Nov. 28, 2024).

U.S. Appl. No. 18/419,923, filed May 1, 2025 Issue Fee Payment.

U.S. Appl. No. 18/419,923, filed Feb. 5, 2025 Notice of Allowance.

U.S. Appl. No. 18/419,923, filed Jan. 8, 2025 Response to Non-Final Office Action.

U.S. Appl. No. 18/419,923, filed Nov. 5, 2024 Non-Final Office Action.

Albalwy et al., "A Blockchain-Based Dynamic Consent Architecture to Support Clinical Genomic Data Sharing (ConsentChain): Proof-of-Concept Study," JMIR Publications 9(11):e27816 (2021) 24 pgs.

Albalwy et al., "A blockchain-based framework to support pharmacogenetic data sharing," The Pharmacogenomics Journal 22:264-275 (2022).

Crosslin et al., "Prospective participant selection and ranking to maximize actionable pharmacogenetic variants and discovery in the eMERGE Network," Genome Medicine 7:67 (2015) 10 pgs.

Fan et al., "Penetrance of Breast Cancer Susceptibility Genes From the eMERGE III Network," JNCI Cancer Spectrum 5(4):pkab044 (2021) 7pgs.

Glicksberg et al., "Blockchain-Authenticated Sharing of Genomic and Clinical Outcomes Data of Patients With Cancer: A Prospective Cohort Study," J Med Internet Research 22(3):e16810 (2020).

Gruendner et al., "Integrating Genomics and Clinical Data for Statistical Analysis by Using GEnome MINIng (GEMINI) and Fast Healthcare Interoperability Resources (FHIR): System Design and Implementation," J Med Internet Res. 22(10): e19879 (2020) 13 pgs.

IBM. What is Blockchain Technology? [Accessed on Apr. 4, 2024].

Jin et al., "Application of a Blockchain Platform to Manage and Secure Personal Genomic Data: A Case Study of LifeCODE.ai in China," J Med Internet Research 21(9):e13587 (2019).

Li et al., "Integration of genetic and clinical information to improve imputation of data missing from electronic health records," JAMIA 26(10):1056-1063 (2019) 8 pgs.

National Human Genome Research Institute. Personalized Medicine. May 2022, updated Apr. 3, 2024. (4 pgs.).

Rogers et al., "Leveraging electronic health record data for clinical trial planning by assessing eligibility criteria's impact on patient count and safety," Journal of Biomedical Informatics 127:104032 (2022) 12 pgs.

Shae et al., "On the Design of a Blockchain Platform for Clinical Trial and Precision Medicine," IEEE pp. 1972-1980 (2017).

* cited by examiner

BLOCKCHAIN SOLUTION FOR HARMONIZED STORAGE OF CLINICAL AND GENETIC DATA

CROSS-REFERENCE TO RELATED APPLICATION

This application is a continuation of U.S. patent application Ser. No. 18/419,923, filed Jan. 23, 2024, which claims the benefit of U.S. Provisional Patent Application No. 63/481,049, filed Jan. 23, 2023, the entire contents of which are hereby incorporated by reference in their entireties.

GRANT INFORMATION

This invention was made with government support under GM147004, and HG010909 awarded by the National Institutes of Health. The government has certain rights in the invention.

BACKGROUND

Precision medicine can be used to provide an accurate diagnosis, appropriate treatment, and timely prevention strategies by considering patients' biological makeup. However, achieving precision medicine can be challenging without integrating clinical and genomics data in a data-sharing framework that achieves large sample sizes. Due to their distinct data types and privacy and data ownership issues, there is a need for systems that integrate clinical and genetic data to avoid missed opportunities.

SUMMARY

The disclosed subject matter provides methods, systems, and blockchain platforms for an improved practice of precision medicine.

According to one embodiment disclosed herein, an example method for practicing precision medicine can include providing, to a blockchain platform, each of clinical data and genetic data, providing the blockchain platform having a first data structure comprising clinical data and a second data structure including genetic data, harmonizing the first and second data structures, creating at least one cohort based on the harmonized first and second data structures, and identifying at least one relationship between the clinical data and the genetic data in each of the at least one cohort.

According to some embodiments, the method can further include querying the blockchain platform wherein a query result can include at least one of the cohorts and the relationship. According to another embodiment, the query can include a query type, and the query type can be at least one of a clinical query, a variant query, and a combination query. According to yet another embodiment, the method can further include querying the blockchain platform, directing the query to a mapping stream, and searching the mapping stream, where the query functions as a search key, returning, via the mapping stream, a query data structure, and searching the query data structure.

As embodied herein, the method can include indexing at least one of the first and second data structures into one of a clinical level, a genetic level, and an access log level. According to some embodiments, the method can include indexing the clinical level into a domain view and a person view. According to yet another embodiment, the method can include indexing the genetic level into a person view, a gene view, and a Minor Allele Frequency (MAF) view.

An example system uses a blockchain platform, which can integrate clinical and genetic data under a unified framework using certain data structures. In certain embodiments, the unified framework can be a secure framework that harmonizes the storage and the querying of clinical and genetic data using blockchain technology. The disclosed subject matter can support combined genotype-phenotype queries, giving a user control of their data, and provide user access logs, improving transparency into how and when health information is used. The disclosed subject matter can have blockchain storage that can be inherently decentralized and secure, giving a user control over how the data is used.

In certain embodiments, the framework uses the Blockchain API MultiChain and its data structures (i.e., streams) to harmonize clinical and genetic data and identify relationships between genetics and clinical symptoms (e.g., Single Nucleotide Polymorphisms related to a target disease). For example, the disclosed system can create specific cohorts based on both clinical and genetic characteristics. The disclosed system can evaluate the relationship and outcomes within the cohorts. In non-limiting embodiments, the combined data can increase statistical power for rare disease analysis enabling the discovery of connections between genetics and clinical observations. For example, the data combined by the disclosed system can increase statistical power for rate disease analysis, allowing discovery between genetics and clinical observations.

In certain embodiments, the disclosed subject matter can support combined genotype-phenotype queries, give institutions decentralized control of their data, and provide user access logs, improving transparency into how and when health information is used.

In certain embodiments, the disclosed subject matter can provide a blockchain platform that can securely store clinical and genetic data. For example, data can be placed on the blockchain itself. The disclosed system can index the data stored on the blockchain using sparse indexing of the data streams. For example, the data can be indexed into three levels: clinical (EHR), genetics, and access logs. Using a mapping stream that can record how data has been indexed and how to retrieve information under all views, the disclosed system can provide improved query time and efficient storage of multimodal data. By harmonizing the storage of the distinct data types, the disclosed system can manage multimodal queries for precision medicine.

DETAILED DESCRIPTION

Reference will now be made in detail to the various exemplary embodiments of the disclosed subject matter, exemplary embodiments of which are illustrated in the accompanying figures. These embodiments and figures are given for the purpose of illustration and not limitation.

Disclosed herein is a decentralized data sharing platform on blockchain technology that unifies clinical and genetic data storage, retrieval, and analysis. The platform can work as a consortium network across multiple participating institutions, each with write and read access. Further, the open-source data-sharing platform, which can use commonly used data formats e.g., the Observational Medical Outcomes Partnership (OMOP) common data model (CDM) and Variant Call Format (VCF) for clinical and genetic data, respectively, can additionally promote data interoperability.

The blockchain API MultiChain can be used to build the platform. MultiChain's novel data structures, also known as "streams," can be leveraged to harmonize clinical and genetic data storage, improve querying efficiency, and flexibility. However, as will be understood by those having skill in the art, the embodiments described herein may be built on other available blockchain APIs and are not so limited to the use of MultiChain. Data streams are an ordered list of items with key-value pairs for database indexing. Indexing data into structured streams improves query time. Disclosed herein are example implementations with an accessible front-end to showcase functionality for building cohorts and identifying genotype-phenotype relationships in a simulated network.

Figure 1:
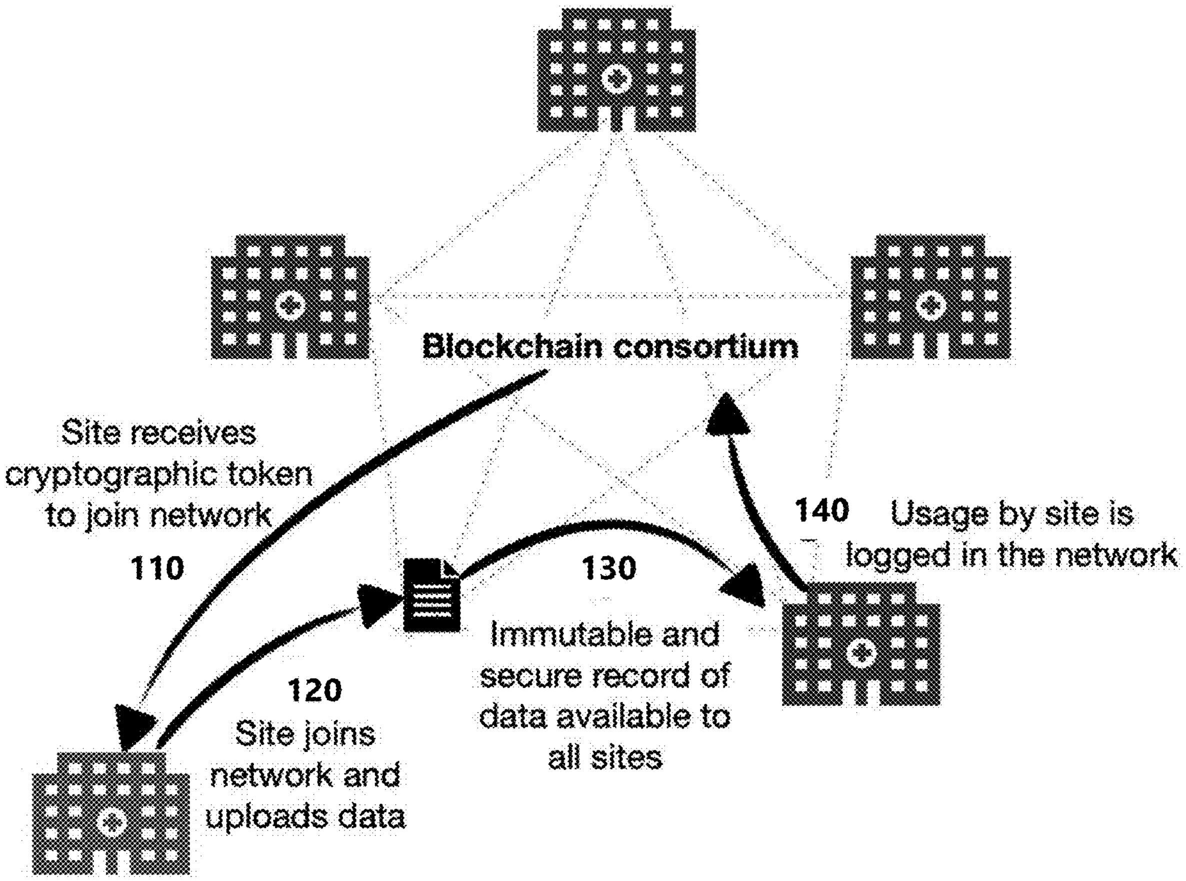
FIG. 1 illustrates a consortium network made up of biomedical institutions.

An open-source blockchain network can allow harmonized storage and efficient retrieval of different levels of patients' genetic and clinical data while recording usage logs. Its query functionality can support a combination of queries that allow searching for clinical and genetic data simultaneously. As is depicted in FIG. 1, such a network can thus be used by a consortium of biomedical institutions that share genetic and clinical data for research purposes. To overcome certain challenges that can be related to blockchain technology, specifically transaction latency and lack of data structures for flexible querying, a sparse indexing of data on top of MultiChain's "data stream" feature can be utilized. In some instances, a 40-fold decrease in query time can be seen, compared to a similar approach which was previously applied to next-generation sequencing data. However, this deeper indexing of streams can slow down data insertion. In some embodiments, insertion can be planned on a monthly or quarterly-basis once data has been transformed and quality checked. During this time, while the network remains active for use, query latency can be increased. This update cadence can mimic certain research data warehouse practice used by certain consortia such as i2b2 and Observational Health Data Sciences and Informatics (OHDSI) network.

As previously explained, FIG. 1 depicts a consortium network made up of biomedical institutions. At 110, a new member institution can receive a cryptographic token to join the network. After receiving the token at 120, the new member institution can join the network and upload its data. Next, at 130, an immutable and secure record of the data from the new member institution becomes available to the other member institutions and vice-versa. At 140, the usage of the network by the new member institution is logged in the network to maintain security and reliability of the data.

As shown in FIGS. 2A-21, data can be indexed into three levels: clinical (EHR) 210, genetics 220, and access logs 230. Within each level, data can be further organized into views. Having multiple views can increase query flexibility as data can be interrogated in different ways. The EHR level 210 can contain Domain 211 and Patient 212 views; the genetics level 220 can include Variant 221, Patient 222, and Gene 223 views, and a Minor Allele Frequency (MAF) counter 224; access logs 230 can contain a single user query view 231. Additional nesting within each view can be used to enable efficient and flexible access to the data.

Further, a mapping stream can be created which records how data has been indexed and how to retrieve information under all views. This can speed up query time and allow for efficient storage of multimodal data under one network, as each stream can be indexed distinctly based on data type. Each entry into the blockchain can contain key-value pairs for querying, a light-weight data object (Javascript Object Notation (JSON object)) to store data, and timestamped metadata to enable encrypted archiving.

OMOP CDM clinical data format is a standardized vocabulary that supports integration of clinical data from multiple sources. OMOP is made up of concepts that represent some unique clinical information (e.g., a specific medication or diagnosis). Under the EHR level 210, two separate indexing schemes can be developed: Domain view 211 and Person view 212. As shown in FIGS. 2A and 2F, the Domain view 211 can be indexed by concept type (e.g., diagnosis, medications, etc). If one queries the network with a concept (e.g., diabetes diagnosis), the network can return all the patients with that record. Furthermore, within each clinical table, the streams can be indexed using the OMOP vocabulary hierarchy. A stream can be created for each high-level concept (ancestor concepts). Other concepts can be assigned to one of these streams based on the ancestor concept that subsumes them in the OMOP vocabulary hierarchy.

Figure 2B:
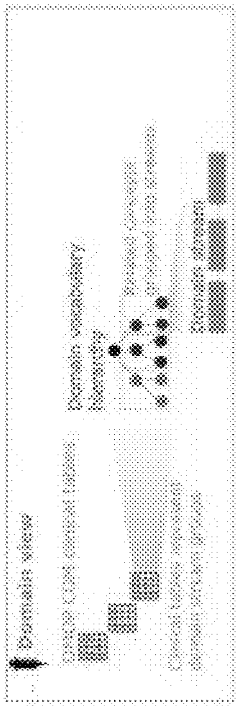
FIGS. 2B and 2F illustrate an example Domain view indexing in accordance with the disclosed subject matter.
Figure 2C:
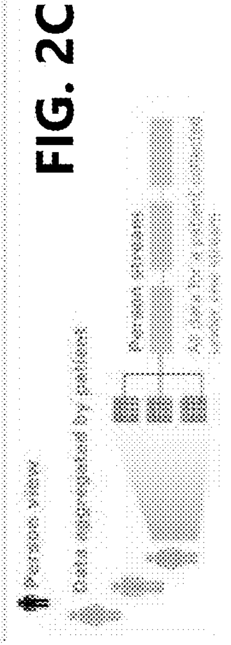
FIGS. 2C and 2G illustrate illustrates an example Person view indexing in accordance with the disclosed subject matter.
Figure 2D:
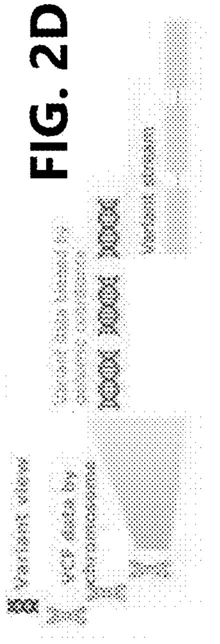
FIGS. 2D and 2H illustrate an example Variant view indexing in accordance with the disclosed subject matter.
Figure 2E:
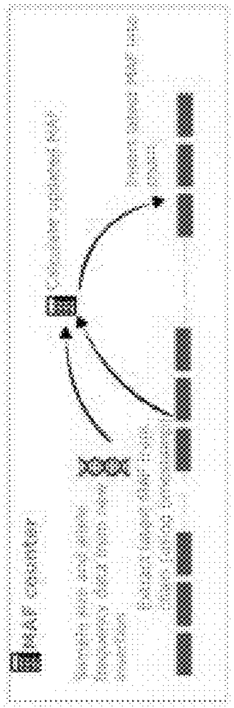
FIG. 2E illustrates an example MAF counter organized by MAF range in accordance with the disclosed subject matter.
Figure 2A:
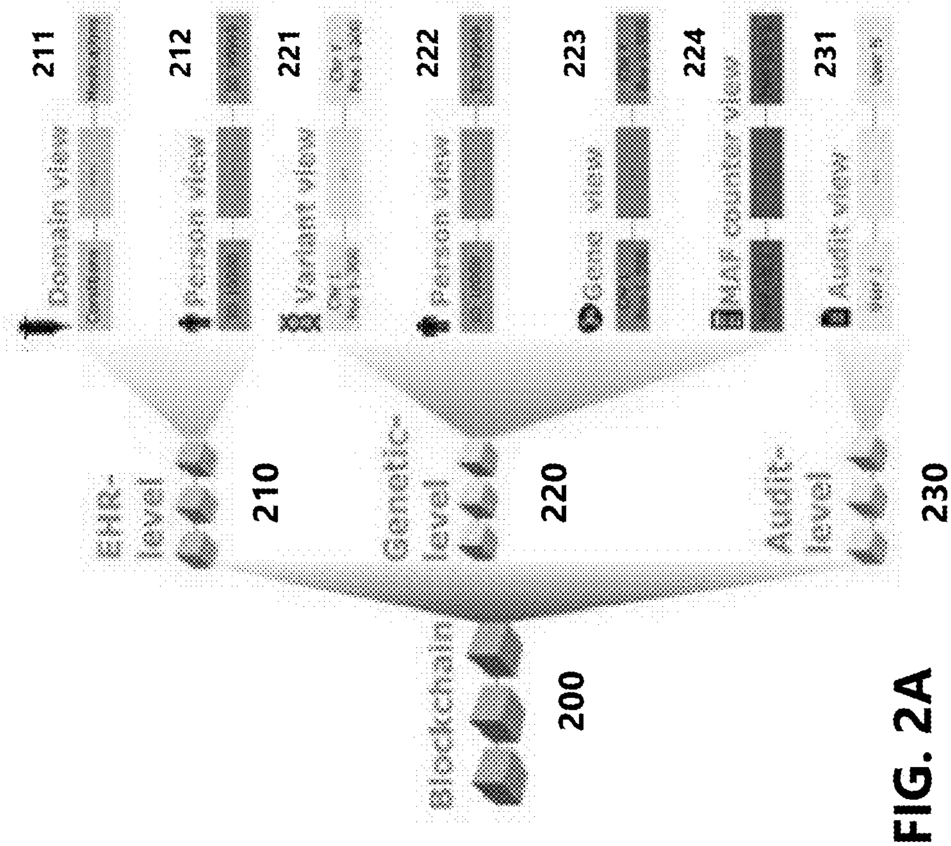
FIG. 2A illustrates example high-level indexing of data in three levels in accordance with the disclosed subject matter.
Figures 2F, 2G, 2H, 2I:
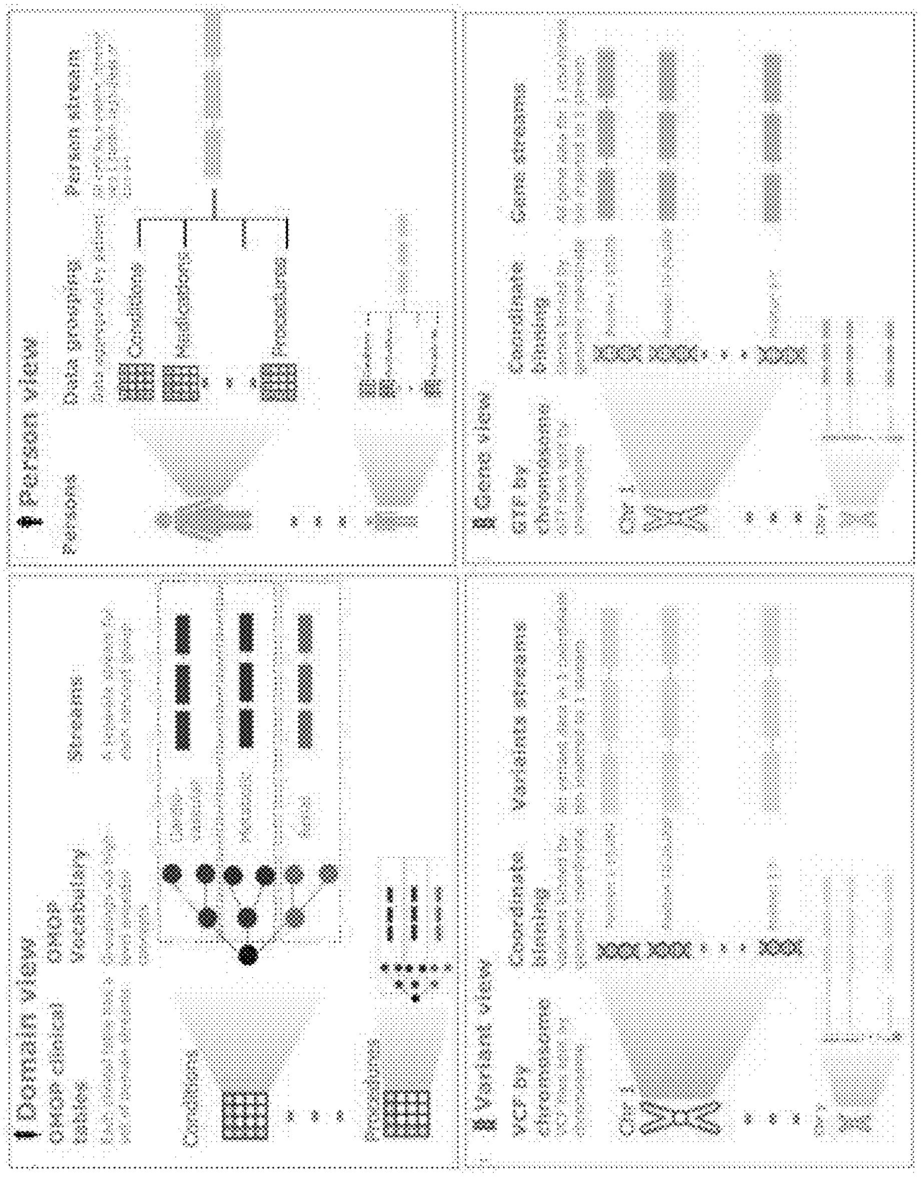
FIG. 2I illustrates the Gene view indexing in accordance with the disclosed subject matter.

As shown in FIGS. 2C and 2G, the Person view 212 can be organized by patient ID, i.e., each data stream contains the entire medical record of a patient to allow quick querying of single patients' medical records. In both views 211, 212, each entry contains several keys that can be used for specifying queries including: patient ID, concept ID, concept type, date of record (i.e., when the clinical event occurred) and concept value or information (e.g., lab value, medication dose etc.). Combining multiple keys in a query can thus enable cohort creation.

A genetic level 220 can be used to store and query genetic variants using the Variant Call Format (VCF). As shown in FIGS. 2A-2I, this level can include four sub-indexing schemes called Variant view 221, Person view 222, Gene view 223, and MAF (minor allele frequency) counter 224. Within the Variant view 221 depicted in FIGS. 2D and 2H, all genetic variants can be logged in the patient population into streams indexed by their genomic coordinate, allowing users to extract patients with a particular variant using genomic locations of the variants. Patient view 222 can create a stream entry per patient and includes all alternative allele variants for the patient, enabling fast retrieval of a patients' genome. Gene view, which is shown in FIG. 21, can store the annotation of the variants, such as whether they overlap with different parts of a gene (e.g., exons, introns).

As shown in FIG. 2E, MAF counter 224 is the most dynamic stream of this level. It can record the MAF values of the variants and is automatically updated as more patients are added to the network. Combining multiple keys in a query enables cohort creation. Additionally, MAF counter is organized by MAF range. MAF calculation occurs at every insertion. Allele frequencies from the newly inserted data are combined with the latest existing MAF data from the MAF counter, and can be verified via time-stamps. The updated MAF is inserted into the MAF counter, becoming the latest calculation available An aspect of controlled access is secure storage and query of audit logs to check for potential misuse, via the use of access logs. In this view, whenever a researcher subscribes to the network or makes any kind of query, the information is automatically logged in a data stream with a timestamp and the user's wallet address, permitting the consortium to keep an immutable record of usage available for review.

One aspect of the framework that cannot be found in other blockchain based solutions is the ability to perform granular queries on the data. Query modules can take advantage of the nested indexing scheme and mapping streams to efficiently retrieve information used for building cohorts and examining relationships. As examples and not limitations, the following queries can be provided in real-time: i) domain queries, such as pulling all patient IDs for individuals diagnosed with a particular disease; ii) patient queries, such as pulling all lab results for a single patient; iii) clinical cohort creation, based on any combination of clinical concepts, concept values, demographics, and date ranges; iv) genetic variant queries, such as pulling all patient IDs that have a specific disease-causing variant; v) patient variant queries, such as pulling the genome of a patient; vi) MAF queries, such as pulling all patients that have rare or common variants (i.e., querying variants with an MAF threshold); vii) gene queries such as pulling all patient IDs who have a disease-causing variant associated with a specific gene of interest; viii) genetic cohort creation based on any combination of genetic variants and MAFs and ix) combination EHR and genetic cohort creation using both clinical and genetic logic gates (e.g., all the patients with the variant X and disease Y; see FIG. 3A) x) combination EHR and genetic queries to identify novel genotype-phenotype relationships within a cohort (e.g., presence of rare variants in a particular gene for patients with disease X compared to controls; see FIG. 3B).

Figure 3A:
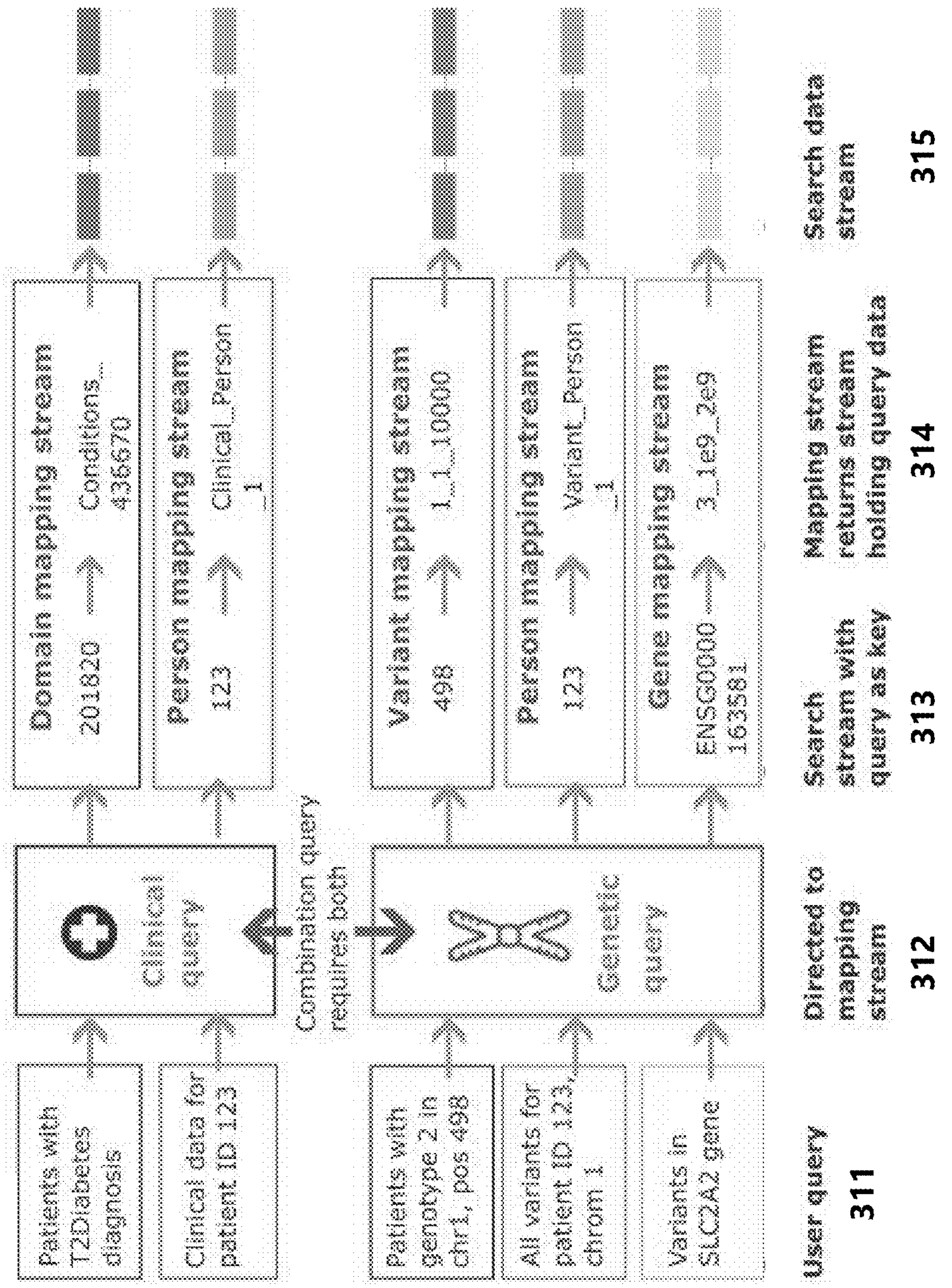
FIG. 3A is a flow chart illustrating an example mapping stream indexing in accordance with the disclosed subject matter.

FIG. 3A depicts a mapping stream index according to example embodiments disclosed herein. At 311, a user query is entered. Based on the users' query, at 312 search keys can be directed to the appropriate stream. At 313, a mapping stream can be created for every view, and entries in the mapping stream can follow a Key: Value structure, wherein the key is the user's input, and the value is the stream where the data is stored. At 314, the mapping stream can return the stream holding query data, and at 315 the data stream can be searched.

Figure 3B:
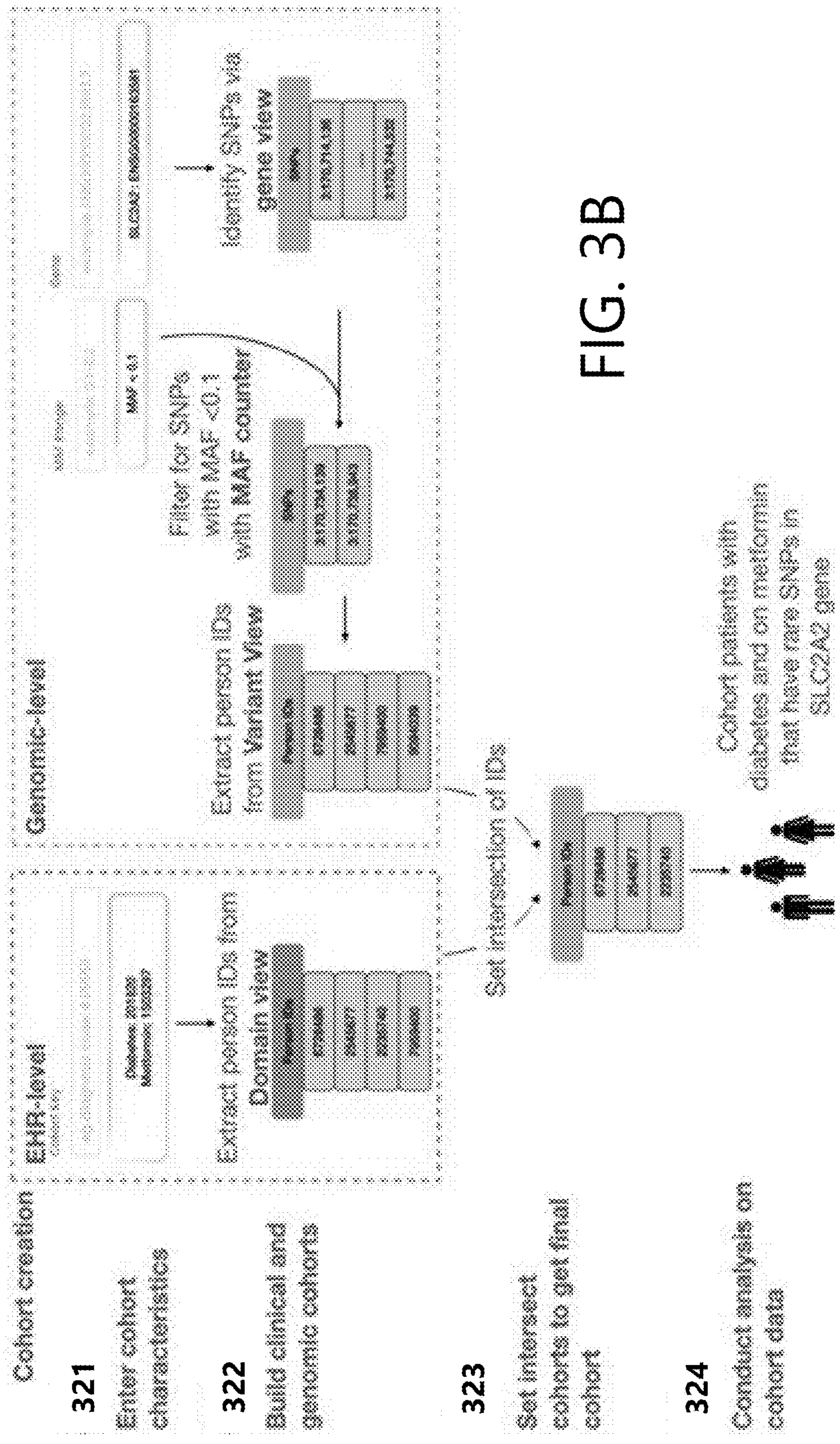
FIG. 3B is a flow chart illustrating an example cohort creation in accordance with the disclosed subject matter.

FIG. 3B depicts the creation of a cohort of patients. According to embodiments disclosed herein, at 321 users can input desired clinical characteristics, genes of interest, and an MAF filter into the search function. Using the EHR-level "Domain view", patient IDs for those that meet clinical criteria can be identified. Using the Genetic-level "Gene, MAF counter, and Variant views," the appropriate variants can be identified and patient IDs with those variants can be extracted, as is shown at 322. At 323, a set intersection of the two cohorts can be done to create a final cohort, which can be analyzed further as is shown in 324.

Figure 3C:
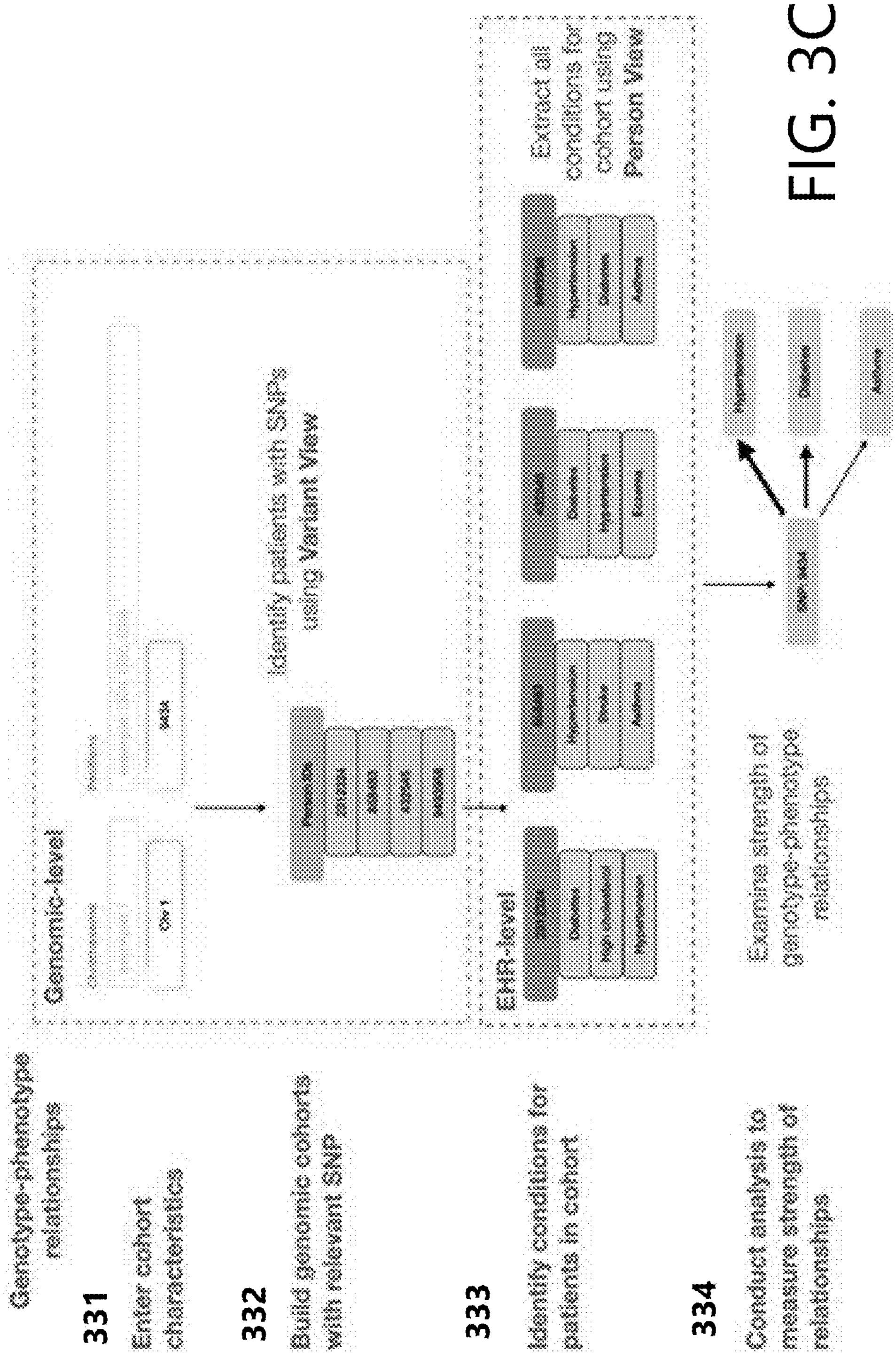
FIG. 3C is a flow chart illustrating example genotype-phenotype relationships in accordance with the disclosed subject matter.

FIG. 3C depicts example relationships between genotypes and phenotypes. As embodied herein and is shown at 331, users can input variants of interest into the search function. Next, at 332, using the Genetic-level "Variant View", IDs for patients with that variant(s) can be extracted. At 333, all diagnoses for each patient are retrieved using the EHR-level "Person view." Finally, at 334, the strength of relationship between each SNP and condition can be examined. "Gene view" can give further information on what genes are carrying the variants, linking the clinical information to detailed genetic information.

Figures 4A, 4B, 4C:
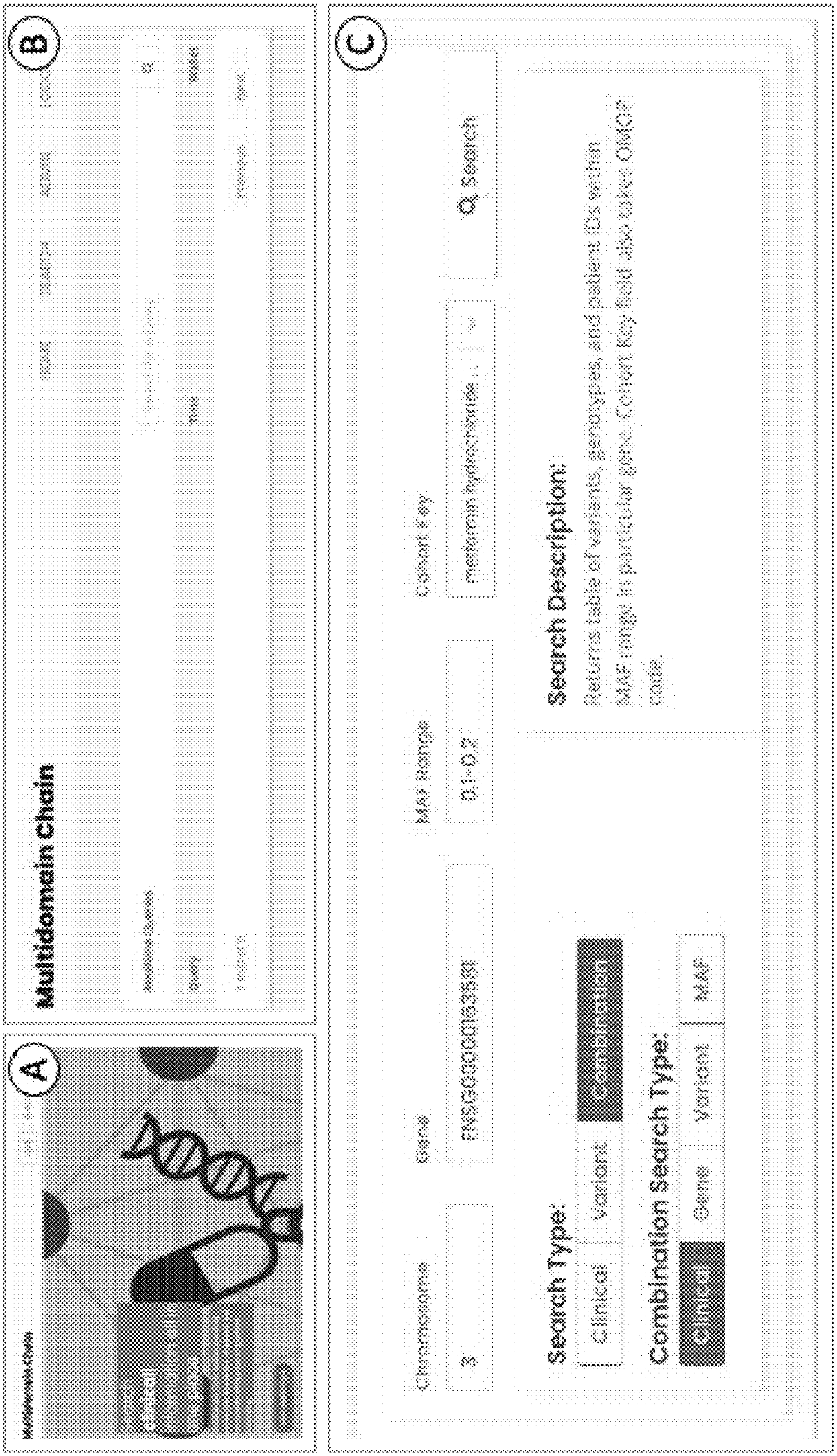
FIGS. 4A-C illustrate various pages of an example graphical user interface for the blockchain platform in accordance with the disclosed subject matter.

A challenge with blockchain technology adoption can be that end-users are not experts in distributed systems or cryptography. As shown in FIGS. 4A-C, an example user-friendly front-end Graphical User Interface (GUI) for researchers can be used to access the network and query data via a website, application, or any other platform. For example, users can sign into the system with a username, and in the back end, the blockchain can recognize the wallet addresses associated with the username and grants access. Users see drop-down menus and search windows in the front end, while all executions will be performed over the blockchain network in the back end. This can increase adoption by abstracting away knowledge of blockchain algorithms while users are querying and analyzing data.

FIGS. 4A-C depict various example interface screens for the GUI described above. More specifically, FIG. 4A depicts an initial landing page which can be displayed to viewers that first access the platform. FIG. 4B depicts an administrative view which can include time-stamped logs of all queries conducted, filtered by user, query type, and/or date. Finally, FIG. 4C depicts a view of the query interface wherein users can query clinical data and/or genetic data.

A data-sharing network can be simulated using publicly available data, e.g., MIMIC-IV and 1000 Genomes Project (https://www.internationalgenome.org/). A patient population can be generated using the 100 anonymized patients available in the MIMIC-IV OMOP dataset and assign an anonymized genome from 1000 Genomes Project to each patient. In doing so, the functionality of a model for combining genetics and clinical data in one infrastructure can be showcased. For example, a cohort of patients can be built, where such patients have a diagnosis of Diabetes, take Metformin, and have a rare variant in the SLC2A2 gene, which is known to influence Metformin response. The availability of genetic and clinical information can allow for the more targeted cohort creation for precision medicine research. Table 1, below, depicts an exemplary but not limiting list of available query types.

TABLE 1

| Query Domain | Query name | Description | Example |
|---|---|---|---|
| Clinical | queryDomain | Query based on OMOP concept ID with date and/or value | Build cohort of patients diagnosed with Diabetes and on Metformin since 2015 |
| | queryPerson | Query based on person ID(s) with date and/or concept and/ or value | Find all medications taken by patient(s) before 2018 |
| Variant | queryVariant | Query based on genomic coordinate and genotype with MAF filter | Find all patients with rare variants (MAF <0.1) in chromosome 8 |
| | queryPerson | Query based on person ID(s) and genomic location with MAF filter | Find all variants with MAF <0.1 for specific patient(s) in chromosomes 11 & 12 |
| | queryVariantGene | Query based on variants associated with particular gene | Find all patients with rare variants in gene BRCA1 |
| Combination | queryClinicalVariant | Query based on clinical cohort definition and gene of interest | Find all patients with rare variants in SOD1 gene and early age of onset ALS |
| | queryVariantClinical | Query based on variants of interest returning patient clinical characteristics | Find all diseases for patients with particular rare variant |

As is shown in Table 1, three example main query types are available in the query module: clinical, genetic and combination. Multiple key searches can be performed in each query using any of the keys included with an entry. For all queries, the mapping stream is first checked to determine the relevant streams to search. Following each query, a call is made to the audit module to record the activity.

The queryDomain functionality can allow for a clinical query based on OMOP concept ID, date of concept ID occurrence and/or concept ID value. For each concept ID in the query, the mapping stream is searched to check for the appropriate stream, where data for that concept is stored. If the concept subsumes child concepts, these are also identified in the mapping stream and searched. Then, the relevant streams are searched with the queries and the relevant patients (person IDs) are returned. Cohorts can be created by specifying multiple concept IDs, values, and date ranges.

The queryPerson functionality can allow for a clinical query based on person ID, concept type (e.g., diagnosis or test), concept ID, date of concept ID occurrence and/or concept ID value. The mapping stream is searched to determine which stream holds the patient's data. All clinical data in that stream that meet the criteria (e.g. person ID, concept type, date, value) can be returned. A particular concept ID or concept type to return (known as the searchKey) can be specified. If this is provided, then only data of that type or ID is returned.

The queryVariant functionality can allows for a genetic query based on the variant of interest's genomic coordinate, genotype, and MAF (optional). For each variant included in the query, the mapping stream is searched to determine the appropriate stream that holds data on that coordinate. The genomic coordinate and genotype are then searched in that stream and patients (person IDs) with the variants of interest are returned. If an MAF range is inputted, variants outside that MAF range are filtered out.

The queryVariantPerson functionality can allow for a genetic query based on Person ID, genetic coordinates (optional), and an MAF filter (optional). The person mapping stream is searched to identify which stream contains the person's genetic data. Once found, that stream is then searched for the queried genetic coordinates and the relevant variants are returned. If an MAF range is inputted, variants outside that MAF range are filtered out.

The query VariantGene functionality can allows for a genetic query based on a gene of interest, genotype, and MAF range (optional). For each gene (based on gene ID) included in the query, the mapping stream is searched to determine the appropriate stream to check. That stream is searched for variants that are associated with the gene. For each variant, patients (person IDs) with the queried genotype are returned. If an MAF range is inputted, variants outside that MAF range are filtered out.

The queryClinicalVariant functionality can allow for a "combination" query based on clinical characteristics, genes of interest, genotype (optional), and MAF range (optional). It returns a cohort (person IDs) of patients with their clinical characteristics and relevant genetic variants. First, a clinical domain query is completed that returns a list of person IDs with the desired clinical characteristics. Second, a genetic query is completed that returns person IDs for patients with relevant variants in the gene of interest (i.e., variants within an MAF range or certain genotype. A set intersection of the two cohorts is done to create a final cohort with both clinical and genetic characteristics.

The query VariantClinical functionality can allow for a "combination" query based on variants and clinical characteristics of interest. First, patients (person IDs) with the queried genetic variants are returned. These IDs are then searched using the clinical Person module to extract relevant clinical characteristics for each person. The characteristics can be aggregated together as summary information.

Embodied herein is a data sharing platform using a consortium blockchain infrastructure. This platform can harmonize genetic and clinical data storage under a unified data format, can natively enable genotype-phenotype queries, and can record user access logs, and can store and share data in a secure and decentralized manner. The stored data can be used for cohort creation and exploration of genotype-phenotype relationships and enables unified sharing of multi-domain data across institutions. The value of this infrastructure is illustrated by a network that can be simulated using publicly available data and make this available to researchers to showcase all querying capabilities, including combination genotype-phenotype queries.

Advantages of a blockchain application will be apparent to those having skill in the art. For example, a blockchain has inherent security safeguards and can cryptographically ensure tightly controlled access, tamper-resistance, and record usage. These safeguards enable data provenance, increased transparency, and enhanced trust. This can be important in distributed data-sharing networks, helping to protect the use of sensitive health data, particularly of marginalized groups.

According to embodiments disclosed herein, the platform can store all data on the blockchain and so reduces the risk of data corruption and tampering as well as allowing more tightly controlled access and usage logs. As blockchains are inherently immutable, data cannot be altered once inserted. This provides protection of data within large-scale data-sharing networks, especially when it is coupled with data access auditing solutions. However, especially with clinical data, as changes to records can be made, an update mechanism is needed. This can be achieved, e.g., with (1) quarterly insertion of data, giving time for clinical data to be corrected before it is uploaded, and (2) use of time-stamps such that latest entries can be selected if multiple entries are returned from a query.

As a framework using blockchain technology, the platform disclosed herein also supports decentralized control of data, allowing greater supervision from patients and communities into how their data is stored and used for research purposes. This can help operationalize equitable data-sharing, a key priority of any precision medicine research program. Through the platform's control parameters, patient and research communities can exert direct control over data access and query rights for their community.

For example, data access can be managed via cryptographic tokens assigned to users' wallets, revoking them after a certain time or specific use has been achieved. An audit system can record all actions by a user on the blockchain, providing an immutable log of all transactions. This can allow patients to inspect the blockchain to learn more about their data, who has access to this data, and how the data has been used. Moreover, access to an immutable log of all system transactions will enable regulators to investigate claims in the event of disputes or misuse. It can also be used to guide future data collection by identifying types of data queries that are most requested by researchers.

The flexible nature of ledger technology allows a wide range of data types from different sources to be stored under one network, enabling harmonized storage of multidomain data. To support this, example novel data structures have been developed using MultiChain. A value of harmonized storage has been demonstrated by the ease at which researchers can make genotype-phenotype queries. Because of this flexibility, data collection can be extended to capture patient-reported and clinical trial outcomes data, in effect making the network a research repository for any healthcare-related data. Further, by using the widely adopted OMOP CDM and VCF file format for clinical and genetic data, respectively, the infrastructure can be easily adopted and scaled by a large number of institutions. It can also open the door to integrating the architecture directly into clinical practice, with all data collected on a patient available to any relevant institution and provider, irrespective of geographic location in a more secure manner.

Storing and querying large-scale data on blockchains can be challenging due to inherent storage redundancy, transaction latency, and a lack of data structures for flexible querying. While the former two can ensure security guarantees, it can also increase computational overhead. Specifically, time and space requirements for storing can be greater than those in certain traditional databases. However, the decentralized control and security safeguards make this an acceptable trade-off, especially given the increasing compute power available to institutions. Another limitation is that all data on a blockchain is made available to all nodes. This can increase privacy risk and means only users verified to access all of the data can be granted read access. Data from users can also be selectively masked.

Further, the consortium blockchain can use a Proof-of-Authority (PoA) consensus mechanism whereby any institution with write access can insert data into the blockchain without approval from other nodes. This contrasts with Proof-of-Work (PoW) where 51% consensus is needed for any data insertion. As institutions must be trusted prior to being granted access, the system is not fully "trust-less." However, this verification requirement generally exists for data-sharing networks, while, in a blockchain, all data insertion and provenance are immutable, allowing easier tracing of malicious actors. The network can also be designed to follow a PoW consensus mechanism if desired, but can slow down the network.

According to some embodiments, the platform disclosed herein can be used with existing precision medicine initiatives, which require a secure and user-friendly data-sharing platform. In unifying multimodal data, a growth in the discovery of novel genotype-phenotype relationships that will translate into improved care. Further, by enabling secure data-sharing with decentralized control, more institutions and communities can be encouraged to participate in biomedical research.

According to some embodiments, the platform can use the blockchain API MultiChain. MultiChain's "data streams" feature can permit a blockchain to be used as a general-purpose database as it enables high-level indexing of the data. The data published in every stream can be stored by all nodes in the network. Each data stream can consist of a list of items. Each item in the stream can contain the following information as a JSON object: a publisher (string), key: value pairs (from 1 to 256 ASCII characters, excluding whitespace and single/double quotes) (string), data (hex string), a transaction ID (string), blocktime (integer), and confirmations (integer). When data needs to be queried or streamed, it can be retrieved by searches using the key: value pairs. Publishing an item to a data stream can constitute a transaction.

The platform can be a private blockchain where network access is limited to consortium members and each joining node requires a token from validators. As it is a semi-private blockchain, a Proof-of-Authority consensus mechanism can be used, whereby any trusted node can validate transactions (e.g., data insertion and token access). Since all data insertion is made public to the consortium members, validating nodes are incentivized to maintain their reputation via accurate and timely data-sharing. Once verified and joined, an institution can subscribe to and query the network as well as contribute data. Auditing can be set up such that institutions receive a summary of their own usage and usage of their contributed data at regular intervals, but they are also able to query the usage in real time using audit view.

As embodied herein, the repositories can contain three module types: buildChain, insertData, and queryData, which will be known to those having skill in the art. buildChain can initialize a MultiChain blockchain including runtime parameters and the access rights for all nodes joining from initialization (i.e., read and write access). The default run-time parameters and node rights can be changed prior to initializing the blockchain. insertData can create the streams and insert the data into the appropriate stream. For all views, a mapping stream can be created. The mapping stream can record how data in the view has been indexed, including what is contained within each stream. insertData has 11 submodules: createStream-Clinical, createStream-Variant, createStream-StructuralVariant, createStream-GTF, insert-Data-Clinical-Domain, insertData-Clinical-Person, insert-Data-Variant, insertData-Variant-Person, insertData-StructuralVariant, insertData-StructuralVariant-Person, insertData-GTF.

In some embodiments, all standardized clinical data tables included in the OMOP CDM can be inserted to the blockchain network. The OMOP CDM can harmonize disparate coding systems into a standardized vocabulary, increasing interoperability and supporting systematic analysis across many sites. To increase efficiency of data querying, two views can be created: domain and person. Domain view can contain data streams organized by concepts. Each row in the OMOP data table can be included as a separate stream item and contain a concept ID (using the OMOP CDM vocabulary), dates (a year, month-year, day-month-year of the clinical record), patient IDs, and result value (if applicable). Concept IDs can be binned using the OMOP vocabulary hierarchy, with a group of related concepts assigned a separate stream.

To achieve this, a number of high-level OMOP concepts can be selected as ancestor concepts (e.g., cardiovascular system, endocrinology system etc.); a stream can be created for each ancestor concept. Every other concept (child concept) can be assigned to a unique ancestor concept (stream). This assignment is based on which ancestor concept subsumes the child concept in the OMOP vocabulary. If a child concept belonged to multiple ancestor concepts, it was assigned one ancestor and this assignment was recorded in the mapping stream. Using the vocabulary hierarchy can ensure that related concepts are grouped together. On average, this can limit the number of streams searched in a single query, improving query times. Patient view can create a stream for a group of patients. Each stream can include the entire medical record of a patient in the stream thereby enabling fast querying of all records from the same patient. As each stream can contain data entries of different domains, it can be viewed similarly to a "noSQL" database in its flexibility. Finally, a mapping stream can keep a record of which stream contains each concept and patient. It can be used by the queryData module when querying.

According to some embodiments, genetic variants (Single Nucleotide Polymorphisms [SNPs], small insertions and deletions [indels], structural variants [SVs]) and the information on the genes that overlap with these mutations can be inserted to the platform. The genetic variant data can be in VCF format and the information on genes can be in GTF format, and four views can be included Variant, Person, Gene, and MAF counter. A mapping stream that records high-level indexing can also be added. The mapping stream can include the stream in which each variant, patient, or gene is stored. Within the Variant view, all genetic variants in the population can be logged into streams indexed by their genomic coordinate.

That is, the genome can be divided into discrete bins with each bin corresponding to a specific genomic coordinate range and a stream is created for each bin. The exact genomic coordinate of the variant, alternative and reference allele, and the genotype can be included as keys for every entry, such that they are queryable. The data field for each entry can include the patients (person IDs) carrying the genotype in each entry. As such, each variant can have multiple entries—one for each genotype (genotype=0, 1, and 2). Patient view can create a stream per patient and include all heterozygous and homozygous alternative allele variants (genotype=1 and 2) for the patient. To reduce storage requirements, homozygous reference alleles (genotype=0) for a patient not stored, but can be automatically recreated when queried, as any variant in the network that was not logged for a specific patient is homozygous reference for that patient.

Gene view can store the annotation of the variants, such as whether they overlap with different parts of a gene (e.g., exons, introns, untranslated regions [UTRs])). Gene view can also include the information on the pathogenicity of the variants in the future. The MAF counter is the most dynamic indexing of this level. It can record the MAF values of the variants and can be automatically updated as more patients are added to the network. Because the blockchain is immutable, a new item with the updated MAF values can be pushed with each insertion. During the insertion, an algorithm can check the timestamp of the existing entries to determine which MAF stream item is the most recent and accurate. It can then extract the relevant information (i.e., sample size and allele frequency for each variant) and combine this with data from the current insertion to determine the new MAF. This can then be inserted into the MAF counter stream.

As disclosed herein, some embodiments can include an access log stream, which is a queryable stream that can store information on each subscription to the network and any analysis command run on the network. A stream item into the access log stream can be created following an activity on the network. This can be achieved by automatically inserting an item into the access log stream with each subscription or query command. By inserting this into the blockchain, an immutable log can be created on the blockchain that can be interrogated. Furthermore, each of the type of query, the dataset (EHR or genetic), timestamp, and user wallet ID can be indexed and stored. Each transaction (i.e., query) can be stored as a single item. The access log can be queried in real-time acting as an alert system for any potential misuse.

As embodied herein, the queryData module can extract information for downstream analysis. To support efficient and multimodal querying, the indexing schema and mapping streams can be leveraged for this module. By indexing all data types into distinct but related streams, and using mapping streams to identify the appropriate streams, the query time can be significantly reduced and enable combination queries. The query module can use the key: value property of stream items to retrieve data from a chain based on a range of defined keys including: concept IDs, concept values, person IDs, dates, genomic locations, genotype, MAF, and genes involved.

When a user queries the chain, they can first specify the query type (clinical, genetic or combined), and query module can then find the correct streams/bins based on the query information. This can be achieved through querying the mapping streams, which contain a record of the data stored in each stream. Once the appropriate stream is identified, the module can extract the data, perform computation if necessary, and return the relevant information. Table 1 (above) describes all the available query functionalities. Overall, queries can be clinical (queryDomain, queryPerson), genetic (queryVariant, query VariantPerson, query VariantGene) or a combination of the two (queryClinicalVariant, query VariantClinical). To increase flexibility and speed of the queries, multiple views with distinct indexes optimized for querying can be included, as is described above.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Thus, the foregoing description of specific embodiments of the disclosed subject matter has been presented for purposes of illustration and description. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents. Furthermore, any features, functions, steps, or elements of the embodiments can be recited in or added to the claims, as well as negative limitations that define the inventive scope of the claims by features, functions, steps, or elements that are not within that scope.

We claim:

1. A method for practicing precision medicine, the method comprising:
- providing, to a blockchain platform, each of clinical data and genetic data;
- providing the blockchain platform having a first data structure and a second data structure;
- identifying at least one relationship between the clinical data and the genetic data;
- wherein at least one of the first data structure and the second data structure is indexed into one of a clinical level, a genetic level, and an access log level; and
- wherein the genetic level is indexed into one or more of a person view, a gene view, and a Minor Allele Frequency (MAF) view.

2. The method of claim 1, further comprising querying the blockchain platform wherein a query result comprises the relationship.

3. The method of claim 2, wherein:
- the query comprises a query type; and
- the query type is at least one of a clinical query, a variant query, and a combination query.

4. The method of claim 1, further comprising:
- querying the blockchain platform;
- directing the query to a mapping stream;
- searching the mapping stream, wherein the query functions as a search key;
- returning, via the mapping stream, a query data structure; and
- searching the query data structure.

5. The method of claim 1, further comprising indexing the clinical level into a domain view and a person view.

6. A system for practicing precision medicine, the system comprising:
- a network capable of providing at least one of clinical data and genetic data;
- a blockchain platform having a first data structure comprising clinical data and a second data structure comprising genetic data;
- wherein the blockchain platform is configured to:
  - identify at least one relationship between the clinical data and the genetic data;
- wherein at least one of the first data structure and the second data structure comprises one of a clinical level, a genetic level, and an access log level; and
- wherein the genetic level comprises one or more of a person view, a gene view, and a Minor Allele Frequency (MAF) view.

7. The system of claim 6, wherein the blockchain platform is further configured to:
- receive a query; and
- return a query result comprising the relationship.

8. The system of claim 7, wherein:
- the query comprises a query type; and
- the query type is at least one of a clinical query, a variant query, and a combination query.

9. The system of claim 6, wherein the blockchain platform further comprises a searchable mapping stream, a search key, and a searchable query data structure.

10. The system of claim 6, wherein the clinical level comprises a domain view and a person view.

11. A blockchain platform for practicing precision medicine, the blockchain platform comprising:
- a first data structure comprising clinical data;
- a second data structure comprising genetic data or clinical data;
- wherein the blockchain platform is configured to:
- identify at least one relationship between the clinical data in the first data structure and the genetic data or clinical data in the second data structure;
- wherein at least one of the first data structure and the second data structure comprises one of a clinical level, a genetic level, and an access log level;
- wherein the clinical level comprises one or more of a domain view and a person view; and
- wherein the genetic level comprises one or more of a person view, a gene view, and a Minor Allele Frequency (MAF) view.

12. The blockchain platform of claim 11, wherein the blockchain platform is further configured to:
- receive a query; and
- return a query result comprising the relationship.

13. The blockchain platform of claim 12, wherein:
- the query comprises a query type; and
- the query type is at least one of a clinical query, a variant query, and a combination query.

14. The blockchain platform of claim 12, further comprising a searchable mapping stream, a search key, and a searchable query data structure.

* * * * *